United States Patent [19]

McKenna et al.

[11] Patent Number: 5,166,360

[45] Date of Patent: Nov. 24, 1992

[54] PROCESS FOR DECREASING COLOR IN BIS-IMIDE FLAME RETARDANTS

[75] Inventors: Michael G. McKenna; Robert M. Moore, Jr., both of Baton Rouge, La.

[73] Assignee: Ethyl Corporation, Richmond, Va.

[21] Appl. No.: 697,027

[22] Filed: May 7, 1991

[51] Int. Cl.$^5$ ............................................ C07D 209/48
[52] U.S. Cl. ................................................... 548/462
[58] Field of Search ............................ 558/1; 514/513; 548/462

[56] References Cited

U.S. PATENT DOCUMENTS

| | | | |
|---|---|---|---|
| 3,873,567 | 3/1975 | Cyba | 548/462 |
| 4,087,441 | 5/1978 | Lee | 548/462 |
| 4,092,345 | 5/1978 | Wolford et al. | 548/462 |
| 4,535,170 | 8/1985 | Sonnenberg | 548/462 |
| 4,873,341 | 10/1989 | Anderson | 548/462 |
| 4,990,626 | 2/1991 | Hutchinson et al. | 548/462 |

OTHER PUBLICATIONS

ASTM D 1925, "Standard Test Method for Yellowness Index of Plastics", (1988).

*Primary Examiner*—Mary C. Lee
*Assistant Examiner*—MarySusan H. Gabilan
*Attorney, Agent, or Firm*—Philip M. Pippenger

[57] ABSTRACT

The yellowness index of a flame retardant N,N'-alkylene-bis-(tetrahalophthalimide), such as N,N'-ethylene-bis-(tetrabromophthalimide), is reduced by treating the bis-imide with strong mineral acid.

12 Claims, No Drawings

PROCESS FOR DECREASING COLOR IN BIS-IMIDE FLAME RETARDANTS

This invention relates to a chemical process which decreases the "yellowness index" of certain halogenated bis-imide flame retardants. More specifically, the invention is directed to decreasing the yellow color of N,N'-alkylene-bis-(tetrahalophthalimide) flame retardants, especially N,N'-alkylene-bis-(tetrabromophthalimide) compounds.

BACKGROUND

Among the halogenated flame retardants, the halogenated bis-imides are particularly useful because the bis-imide structure confers good thermal stability to the flame retardant, and its incorporation does not detract from the thermal stability of materials such as plastics in which it is used. Moreover, the bis-imides are resistant to photo-degradation. A negative aspect associated with these materials is that they tend to exhibit varying degrees of yellowness. This factor makes them unacceptable for use as flame retardants in certain, especially white, polymeric materials. In addition, the color of a given bis-imide tends to vary from batch to batch. This makes it difficult for a plastics manufacturer to maintain consistency in the colors of his products. The yellow color is believed to be due to the introduction of small amounts of unidentified colored impurities, i.e., "color bodies," during the manufacturing process. In the context of the instant invention, "yellowness index" is determined according to the procedure set forth in ASTM D-1925, entitled "Yellowness Index in Plastics."

U.S. Pat. No. 3,873,567 discloses that N,N'-alkylene-bis-(tetrahalophthalimides) can be used as flame retardants. These compounds can be prepared by imidization of the corresponding halogenated phthalic anhydride with an alkylenediamine in solution using an organic solvent system, but for reasons of cost and safety, an aqueous medium has been preferred. U.S. Pat. No. 4,087,441 discloses the preparation of N,N'-alkylene-bis-(tetrahalophthalimide) compounds in an aqueous suspension, and U.S. Pat. No. 4,092,345 discloses the use of water, along with an alkyl organic acid. In this latter case, the reaction proceeds via an alkylene diammonium-bis-(tetrahalophthalate) salt, which can be isolated. Heating the salt produces the desired ring-closed bis-imide.

Many of the variants of the imidization process carried out in aqueous acid give a solid N,N'-alkylene-bis-(tetrahalophthalimide) which is not the desired white color exhibited by the pure compound, but rather is yellow to one degree or another. Clearly, there is a need for a method to eliminate, or at least decrease, the yellow color associated with N,N'-alkylene-bis-(tetrahalophthalimide) flame retardants.

SUMMARY OF THE INVENTION

Accordingly, it is one objective of this invention to provide a method for decreasing the yellowness index of an N,N'-alkylene-bis-(tetrahalophthalimide), especially an N,N'-alkylene-bis-(tetrabromophthalimide) such as N,N'-ethylene-bis-(tetrabromophthalimide). It is a second objective of this invention to provide the aforesaid improvement in color within the context of the known process for making N,N'-alkylene-bis-(tetrahalophthalimides) in aqueous acid. Other objectives of the invention will become apparent hereinafter.

In attaining the aforesaid objectives, this invention provides a method for reducing the yellowness index of a yellowed N,N'-alkylene-bis-(tetrahalophthalimide), which may have been, but need not be, produced in aqueous acid, which process comprises first slurrying the bis-imide in a strong mineral acid, recovering the bis-imide, washing the recovered bis-imide with aqueous base to substantially remove the acid, and then optionally drying the recovered bis-imide.

The process of this invention, as well as the manner in which it is carried out, will become evident by reference to the following description, including the specific Examples.

DETAILED DESCRIPTION

The method of this invention can be practiced on any N,N'-alkylene-bis-(tetrahalophthalimide), e.g., those which are flame retardants. Such bis-imides include, for example, N,N'-methylene-bis-(tetrahalophthalimide), N,N'-ethylene-bis-(tetrahalophthalimide), N,N'-isopropylene-bis-(tetrahalophthalimide), and other lower alkylene-bis-imides, where "lower alkylene" means a straight or branched chain $C_1$ to $C_6$ alkylene group. The term "halo" as used herein means chlorine or bromine. The preferred bis-imides carry bromine. Among the various bis-imides upon which the invention can be practiced, N,N'-ethylene-bis-(tetrabromophthalimide) and N,N'-methylene-bis-(tetrabromophthalimide) are preferred reactants, and the method is especially useful when the bis-imide is N,N'-ethylene-bis-(tetrabromophthalimide). The results are most pronounced when the N,N'-alkylene-bis-(tetrahalophthalimide) has been produced by imidization in an aqueous acid, such as acetic or propionic acid, since this preparative method tends to produce a bis-imide in which the yellow coloration is most pronounced.

The yellowed bis-imide is first slurried in concentrated mineral acid. The terms "slurried" and "slurrying" used herein both mean creating a suspension of the generally solid bis-imide in the acid and stirring it. Although several of the strong mineral acids may be employed, for reasons of cost and availability it is preferred that the mineral acid be sulfuric acid. Although some dilution with water is permissible, it is also preferred that the acid be concentrated sulfuric acid, i.e., about 96–98%. Oleum, e.g., concentrated sulfuric acid containing about 28 percent dissolved $SO_3$, can also be employed effectively.

Although the relative amounts of the bis-imide and mineral acid in the slurry can vary, sufficient acid should be used to create a suspension. In general, the bis-imide can comprise about 5 wt% to about 30 wt% of the slurry. The slurrying can be carried out at ambient temperature, but it is often advantageous to heat the slurry to a temperature in the range of about 150° C. to about 225° C. for a period of time; for example, 10 hr to 4 hr, respectively.

The acid-treated bis-imide is recovered from the slurry. The recovery is readily effected by filtration or centrifugation. The recovered bis-imide is then washed with water and aqueous base to remove traces of the acid. This can be done on the filter or centrifuge. The effectiveness of the washing can be ascertained by monitoring the pH of the filtrate or centrifugate. Although various bases, such as sodium hydroxide and sodium bicarbonate, can be employed to neutralize the acid traces, the use of ammonium hydroxide is preferred because it is easier to handle and leaves less residual salt in the bis-imide.

After the bis-imide has been washed, it is recovered from the filter or centrifuge if necessary and optionally dried. The combination of drying time with drying temperature can be varied, but drying at a temperature in the range of about 80° C. to about 250° C. for about 12 hr to about 4 hr, respectively, is generally sufficient. If the bis-imide is to be employed in another process it may not be necessary to dry it.

The following represent preferred embodiments of the invention. Other embodiments of the invention can be practiced by extension of the principles set forth herein.

EXAMPLE 1

To a 1-L resin kettle equipped with a reflux condenser, a mechanical stirrer, and a thermometer attached to a Thermowatch unit, was charged 90 g of yellowed N,N'-ethylene-bis-(tetrabromophthalimide), which had been prepared in aqueous propionic acid, substantially as described in U.S. Pat. No. 4,092,345, and had a yellowness index greater than 35. Also charged was 400 ml concentrated sulfuric acid. The heterogeneous mixture was heated with stirring (i.e., "slurried") at 180° C., during which period the color of the solid deepened; after about 5 hr, however, the solid became much lighter in color. After heating and stirring for a total of about 9 hr, the slurry was allowed to cool to ambient temperature, and then the solid was recovered by filtering the slurry. The recovered N,N'-ethylene-bis-(tetrabromophthalimide) was washed on the filter successively with water, dilute aqueous ammonium hydroxide, and water again until the filtrate was substantially neutral (pH abt. 7). The washed bis-imide was transferred to a crystallization dish and dried in an oven at 225° C. for 6 hr. The dried N,N'-ethylene-bis-(tetrabromophthalimide) weighed 86.8 g, representing 96% recovery. The yellowness index of the product was 15. Thermogravimetric analysis indicated a 3% weight loss to 300° C.

EXAMPLE 2

N,N'-Ethylene-bis-(tetrabromophthalimide), which had a yellowness index of about 35 (deep yellow), was soaked in oleum (28 wt% $SO_3$) overnight at ambient temperature. The bis-imide was recovered by vacuum filtration on a fritted glass funnel. The recovered bisimide was washed on the funnel with water and then dilute aqueous ammonium hydroxide. The washed bisimide, which was light yellow in color, was dried at 100° C. The dried bisimide was oven-aged overnight at 220° C., causing a 5% weight loss. The oven-aged product was near white (yellowness index 23). Thermogravimetric analysis of the product showed a weight loss of 8% up to 350° C.

It will be evident that the principles set forth above in the preferred embodiments can readily be extended to the treatment of other bis-imides within the scope of the following claims.

We claim:
1. A method for reducing the yellowness index of a yellowed N,N'-alkylene-bis-(tetrahalophthalimide), which process comprises
   (a) forming a slurry consisting essentially of the yellowed N,N'-alkylene-bis-(tetrahalophthalimide) and strong mineral acid;
   (b) recovering the N,N'-alkylene-bis-(tetrahalophthalimide) from the slurry; and
   (c) washing the recovered N,N'-alkylene-bis-(tetrahalophthalimide) with aqueous base to substantially remove the acid.

2. The method of claim 1 further comprising the step of drying the washed N,N'-alkylene-bis-(tetrahalophthalimide).

3. The method of claim 1 wherein said N,N'-alkylene-bis-(tetrahalophthalimide) is an N,N'-(lower alkylene)-bis-(tetrabromophthalimide).

4. The method of claim 3 wherein said N,N'-(lower alkylene)-bis-(tetrabromophthalimide) is selected from N,N'-methylene-bis-tetrabromophthalimide) and N,N'-ethylene-bis-(tetrabromophthalimide).

5. The method of claim 4 wherein said N,N'-(lower alkylene)-bis-(tetrabromophthalimide) is N,N'-ethylene-bis-(tetrabromophthalimide).

6. The method of claim 1 wherein said strong mineral acid is selected from concentrated sulfuric acid and oleum.

7. In a process which produces a yellowed N,N'-alkylene-bis-(tetrahalophthalimide) in aqueous acid, the improvement therein which comprises
   (a) slurrying the yellowed N,N'-alkylene-bis-(tetrahalophthalimide) in strong mineral acid;
   (b) recovering the N,N'-alkylene-bis-(tetrahalophthalimide) from the slurry; and
   (c) washing the recovered N,N'-alkylene-bis-(tetrahalophthalimide) with aqueous base to substantially remove the acid;
whereby the yellowness index of the N,N'-alkylene-bis-(tetrahalophthalimide) is decreased.

8. The method of claim 7 further comprising the step of drying the washed N,N'-alkylene-bis-(tetrahalophthalimide).

9. The method of claim 7 wherein said N,N'-alkylene-bis-(tetrahalophthalimide) is an N,N'-(lower alkylene)-bis-(tetrabromophthalimide).

10. The method of claim 9 wherein said N,N'-(lower alkylene)-bis-(tetrabromophthalimide) is selected from N,N'-methylene-bis-(tetrabromophthalimide) and N,N'-ethylene-bis-(tetrabromophthalimide).

11. The method of claim 10 wherein said N,N'-(lower alkylene)-bis-(tetrabromophthalimide) is N,N'-ethylene-bis-(tetrabromophthalimide).

12. The method of claim 7 wherein said strong mineral acid is selected from concentrated sulfuric acid and oleum.

* * * * *